US008383040B2

(12) United States Patent
Schosnig et al.

(10) Patent No.: US 8,383,040 B2
(45) Date of Patent: Feb. 26, 2013

(54) ANALYTICAL TEST TAPE INSTRUMENT

(75) Inventors: Stefan Schosnig, Hirschberg-Grosssachsen (DE); Ingmar Barthold, Salach (DE); Ulrich Kehr, Gartringen (DE); Andree Treinzen, Heimshelm (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 58 days.

(21) Appl. No.: 13/087,905

(22) Filed: Apr. 15, 2011

(65) Prior Publication Data
US 2011/0236276 A1  Sep. 29, 2011

Related U.S. Application Data

(63) Continuation of application No. PCT/EP2009/063618, filed on Oct. 16, 2009.

(30) Foreign Application Priority Data

Oct. 20, 2008 (EP) .................................. 08167032

(51) Int. Cl.
*G01N 21/00* (2006.01)
(52) U.S. Cl. ......................................................... 422/66
(58) Field of Classification Search .................. 422/66
See application file for complete search history.

(56) References Cited

U.S. PATENT DOCUMENTS

| 3,556,534 | A | * | 1/1971 | Bara et al. ................. 360/78.02 |
| 4,014,747 | A | * | 3/1977 | Kenyon ..................... 435/287.1 |
| 4,922,353 | A | * | 5/1990 | Inoue ........................ 360/96.51 |
| 5,742,142 | A | * | 4/1998 | Witt ............................... 318/599 |
| 6,138,346 | A | * | 10/2000 | Shutts et al. ..................... 29/758 |
| 2003/0162912 | A1 | * | 8/2003 | Disch et al. ................... 525/539 |
| 2006/0229531 | A1 | * | 10/2006 | Goldberger et al. .......... 600/573 |
| 2008/0103415 | A1 | | 5/2008 | Roe et al. |

FOREIGN PATENT DOCUMENTS

| DE | 20 2007 003 419 | 5/2007 |
| EP | 1 760 469 A1 | 3/2007 |
| EP | 1 936 374 A1 | 6/2008 |
| GB | 1 485 506 | 9/1977 |
| WO | WO 2006/000792 A1 | 1/2006 |

* cited by examiner

*Primary Examiner* — Lore Jarrett
(74) *Attorney, Agent, or Firm* — Krieg Devault LLP

(57) ABSTRACT

An analytical test tape instrument includes an exchangeable test tape unit which comprises a test tape provided with a plurality of test elements to which body fluid can be applied. The test tape instrument also includes a tape drive that can be coupled with the test tape unit to wind the test tape so that the test elements can be successively made available at an application site. The tape drive has a direct current motor and a reduction gear unit arranged between the direct current motor and the test tape unit.

24 Claims, 2 Drawing Sheets

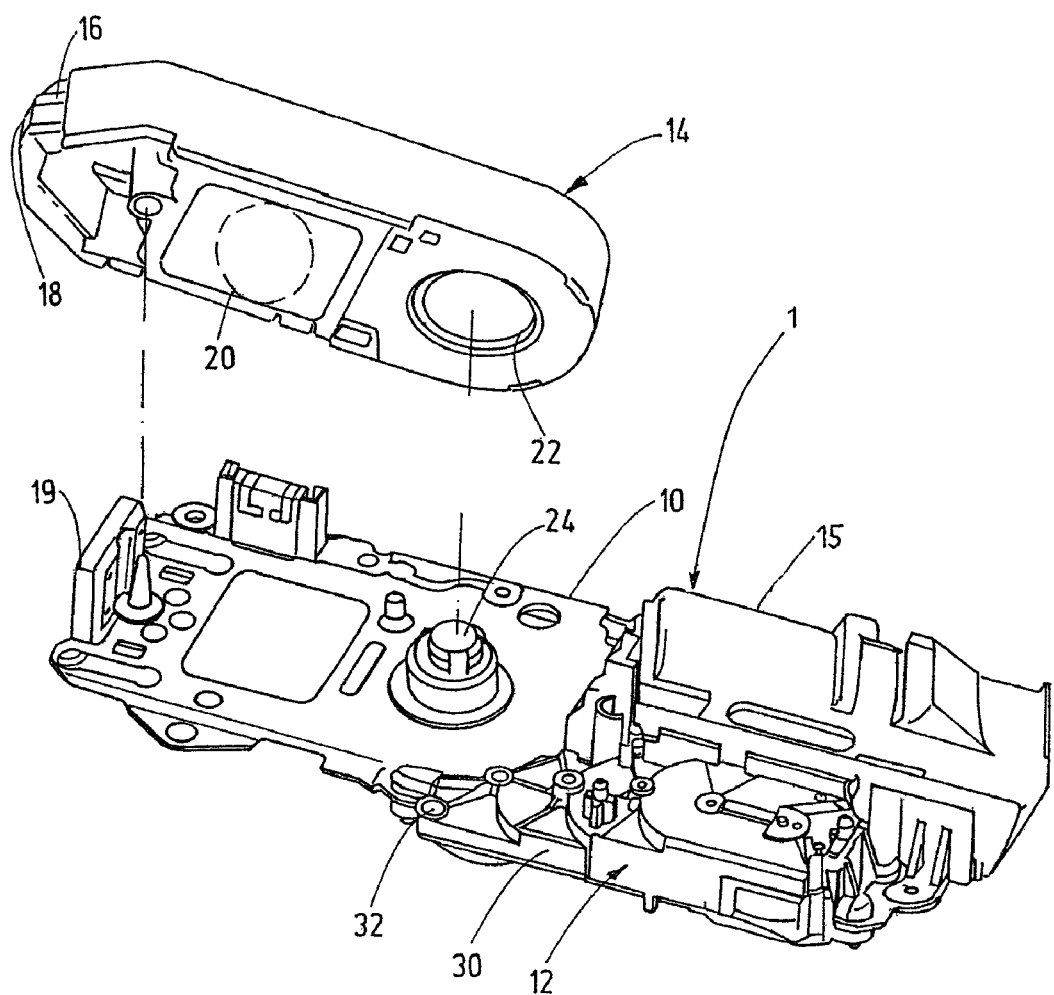
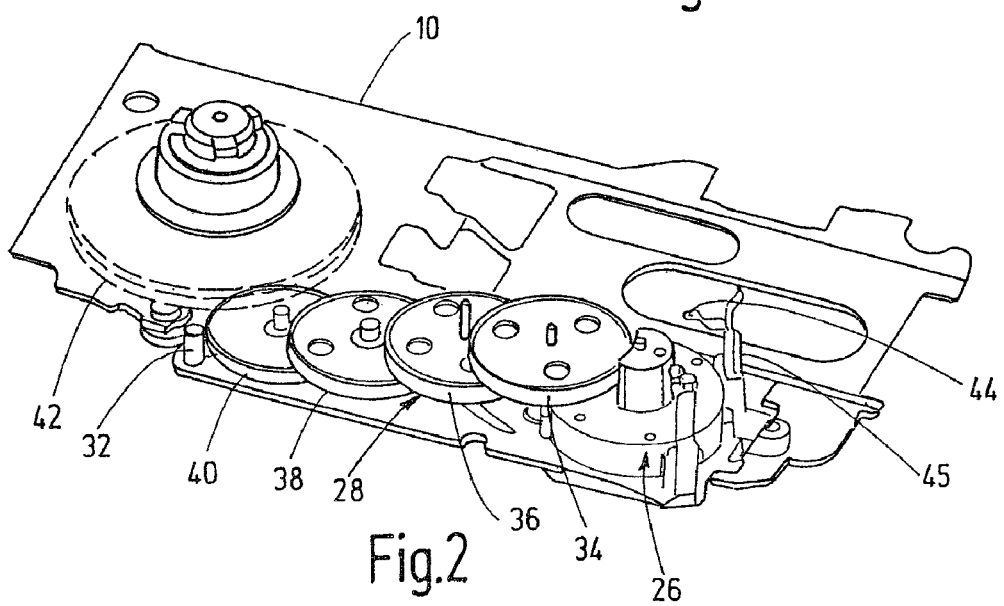

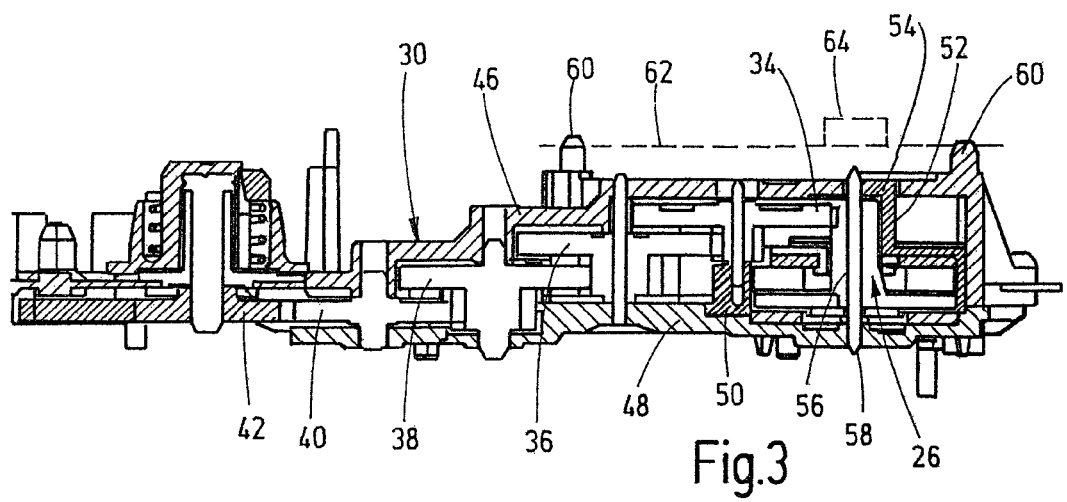

ANALYTICAL TEST TAPE INSTRUMENT

CROSS-REFERENCE TO RELATED APPLICATIONS

This application is a continuation of International Application No. PCT/EP2009/063618 filed Oct. 16, 2009, which claims priority to EP Application No. 08167032.5 filed Oct. 20, 2008. Each of the referenced applications is incorporated herein by reference in its entirety.

FIELD OF THE INVENTION

The invention concerns an analytical test tape instrument such as a hand-held device for blood sugar tests. The test tape instrument includes an exchangeable test tape unit, such as a tape cassette, which comprises a test tape provided with a plurality of test elements to which body fluid can be applied, and a tape drive that can be coupled with the test tape unit to wind the test tape so that the test elements can be successively made available at an application site.

BACKGROUND

Test tape systems have already been proposed in a number of patent applications from the applicant in order to gain further advantages for the user compared to the strip systems on the market. In addition to a reliable positioning of the test elements, it is also necessary for practical purposes to ensure that their on the spot use is not impaired by excessive noise development.

On this basis it is desireable to further improve the systems proposed in the prior art and to achieve a reliable test element positioning with little interfering noise in a compact assembly.

SUMMARY

According to one aspect, an analytical test tape instrument is provided. In one form, the test tape instrument is for blood sugar tests. The test tape instrument includes an exchangeable test tape unit that is, in one embodiment, in the form of a tape cassette. The test tape unit comprises a test tape provided with a plurality of test elements to which body fluid can be applied, and a tape drive that can be coupled with the test tape unit to wind on the test tape so that the test elements can be successively made available at an application site. The tape drive has a direct current motor and a reduction gear unit arranged between the direct current motor and the test tape unit.

The analytical test tape unit is based on the idea of using a compact high-speed motor. Accordingly it is proposed that the tape drive has a direct current motor and a reduction gear unit arranged between the direct current motor and the test tape unit. The direct current motor can be readily integrated into a hand-held device due to its small installation space and low energy requirement and it enables a low-noise and low-vibration operation while the reduction gear unit ensures a suitable rotational speed/torque conversion for reliable tape positioning. A simplified manufacturing process combined with a cost-effective construction method is another advantage.

The direct current motor is in the form of a mechanically commutated thin-profile rotor in order to achieve a uniform noise behavior with little torque variation. Also such a motor can be simply constructed from a few parts and it is particularly suitable for battery operation. It would also be conceivable to use an electronically commutated direct current motor.

Another improvement with regard to interfering noises and contamination can be achieved by encapsulating the reduction gear unit together with the direct current motor against the environment in a gear housing. A particularly compact and precise assembly can be achieved in that the direct current motor has a motor housing sections of which are formed by a housing wall of the gear housing.

Another embodiment provides that the rotor of the direct current motor has a bearing located in the gear housing. This allows a further shortening of the tolerance chains in connection with the downstream gear unit. Another improvement in this embodiment arises as a result of the fact that the direct current motor has a bearing for its rotor located in a motor housing member and that the motor housing member is clamped in the gear housing. The gear member of the reduction gear unit which is directly coupled with the direct current motor can be mounted in a housing section of the direct current motor. In order to avoid acoustic bridges to the body, the test tape unit can be put on an instrument chassis, wherein the gear housing is only connected at certain points to the instrument chassis while keeping an air gap clear.

In order to be able to reliably transmit the drive forces, the reduction gear unit can be in the form of a toothed-wheel gear unit and in particular a multistep spur gear unit with, for example, a laterally offset input and output. In this connection a cost-effective production can be provided when the gear wheels of the toothed-wheel gear unit include injection-molded parts made of plastic, in particular polyoxymethylene (POM).

In order to transport the test tape as uniformly as possible independently of the diameter of the spool, the tape drive can have a speed controller to control the rotational speed of the direct current motor depending on the number of test elements of the test tape unit which have been provided. Another embodiment provides that the motor rotational speed of the direct current motor is in a range between 100 and 200 revolutions/s and that the output rotational speed of the reduction gear unit is between 0.2 and 0.5 revolutions/s. The direct current motor can be connected via brushes to a battery-powered energy supply, wherein brush holders are integrated in the gear housing to dampen brush vibrations.

Motor vibrations can be further minimized by providing the direct current motor with a motor shaft that has a longitudinally slotted end section so that the slotted end section can be inserted into a bearing bore with tolerance compensation.

When the motor shaft of the direct current motor is configured as one piece together with a drive pinion made of plastic, in particular POM, reduced bearing friction and correctness of the angle of motion transmission is provided.

The tape drive described herein is, apart from noise reduction, also compact in design. Accordingly it is possible that a housing encasing the tape drive and accommodating the test tape unit encloses a constructed space of less than 150 $cm^3$, or less than about 135 $cm^3$.

The tape drive can be configured to rotate a take-up spool of the tape cassette to wind up the test tape provided with the test elements. Thereby, used test elements can be easily disposed.

BRIEF DESCRIPTION OF THE WINGS

The invention is further elucidated in the following on the basis of an exemplary embodiment shown in the drawings.

FIG. 1 shows an analytical test tape instrument with an exchangeable tape cassette in a perspective view.

FIG. 2 shows the tape drive of the test tape instrument in an enlargement of a section of FIG. 1.

FIG. 3 shows a profile of the tape drive along a line of intersection running through the axes of rotation of the gear wheels.

FIG. 4 shows the motor of the tape drive in an axial section.

FIG. 5 shows the motor shaft slotted at the end in a perspective sectional enlargement of FIG. 4.

DETAILED DESCRIPTION

The test tape instrument shown in FIG. 1 comprises an instrument unit 1 with a tape drive 12 designed to be particularly smooth running and an exchangeable tape cassette 14 which can be coupled with the tape drive. For the sake of clarity, the chassis of the instrument unit 1 is shown only with a section of the encasing housing 15. The test tape instrument can be used as a hand-held device for blood sugar measurements which can be carried out on the spot by the user. Details on this can for example be derived from EP-A 1 760 469, which is incorporated herein by reference.

The tape cassette 14 shown in FIG. 1 from below in a rotated perspective contains a test tape 16, sections of which are provided with test fields 18 to the front side of which blood or body fluid can be applied in the area of a deflecting tip as an application site. At the same time the test field 18 can be measured at this site from the rear side by means of the measuring unit 19. For this purpose the test tape 16 is wound from a take-off spool 20 onto a take-up spool 22 so that the test fields 18 that are spaced apart from one another can be successively brought into use at the application site for successive tests. In this connection only the take-up spool 22 is driven by the drive pin 24 which engages in a form-locking manner.

As can also be seen in FIG. 2 the tape drive 12 has an electric motor in the form of a direct current motor 26 and a downstream reduction gear unit 28. The reduction gear unit 28 is encapsulated and screened against the environment together with the motor 26 in a gear housing 30. In order to suppress structure-borne noise, the gear housing 30 is only connected to the underlying chassis 10 at a few attachment points 32 while keeping an air gap free.

The gear housing is formed from an LCP (liquid crystal polymer) i.e. a high-melting material which allows narrow tolerances. Where appropriate other superstructures on the chassis 10 also are made of this material in order to ensure corresponding coefficients of linear expansion.

The reduction gear unit 28 includes several gear wheels 34, 36, 38, 40 with rotary axes that are parallel to one another which as a multistep spur gear unit thus have a laterally offset input and output. Another gear wheel 42 on the underside of the chassis 10 is coaxially connected to the drive pin 24. The gear wheels can be injection-molded parts made from POM (polyoxymethylene). With regard to further noise reduction, the depth of tooth of the first gear wheel 34 that engages with the rotor is increased so that the teeth are designed to be somewhat longer. As a result the teeth are less stiff and thus dampen vibrations.

In order to further limit an unintentional transmission of sound, the motor 26 is supplied with energy via vibration-cushioned brushes 44. For this purpose brush holders 45 of sufficient stiffness are integrated in the gear housing 30 in order to avoid high vibration frequencies. In addition, parts of the brushes 44 can also be provided with grease in the area of the lower case 48 in order to dampen especially high frequency vibrations.

As can be seen in FIG. 3, the gear housing 30 has an upper case 46 and a lower case 48 between which the gear wheels 36, 38 and 40 are mounted. In contrast, the downwards projecting axis of the first gear wheel 34, which is directly coupled with the motor 26, is mounted in a housing member 50 of the motor housing 52 such that positioning tolerances are substantially minimized there. A further dome-shaped motor housing member 54, which forms the upper bearing for the motor rotor 56, is firmly clamped in an opening of the upper case 46 in order to ensure an exact centering and stabilization also at this position.

The motor housing 52 is not closed on all sides but rather its end face is open towards the bottom in order to create the most compact possible arrangement. The opening is covered by the lower case 48 which thus completes the motor housing and forms a bearing 58 for the rotor 56.

The upper case 46 is connected via point connections 60 with a control circuit board 62 which is only shown symbolically and has a rotational speed controller 64 for the motor 26. In this manner the rotational speed of the motor can be controlled in accordance with the spool diameter depending on the number of used tests in such a manner that a constant tape transport speed of about 15 mm/s is achieved. In this connection the motor speeds are in a range of about 100 to 200 revolutions per second whereby the required torque is also available due to the reduction to an output speed of the drive pin 24 of about 0.2 to 0.4 revolutions per second.

As shown best in FIG. 4 the motor shaft 66 and a pinion 68 are formed from plastic, in particular POM, in one piece where the pinion meshes with the first gear wheel 34. The iron-free rotor results in a dwell momentum-free operation in addition to high dynamics. A mechanically commutated thin-profile rotor 70 is used for the rotor which, in addition to a small overall length, has a low starting voltage with a low energy consumption which is of particular advantage in a portable instrument for battery operation.

The lower bearing 58 of the rotor 56 is formed by a bore in the lower case 48. As shown in the detailed view of FIG. 5, the motor shaft 66 can have an end section 72 that is longitudinally slotted and can be inserted by radial spreading with tolerance compensation into the bearing bore in order to ensure a particularly quite running. In this connection one should bear in mind that in this area vibrations of the motor shaft lead to a high noise emission whereas in the upper section of the shaft the gear wheel forces result in a preferred orientation in the bearing.

Especially the first gear wheel 34, which rotates at high speed, is subjected to a radial force in a preferred orientation due to the meshing. In order to improve the bearing conditions in this connection, a hub with a prismatic guide for the gear shaft can be provided instead of a cylindrical bearing bore.

The compact tape drive 12 also allows the instrument housing 15 to be very small. The enclosed instrument volume comprises about 135 cm$^3$ whereas an additionally coupled lancing aid (optional, not shown) has a constructional volume of about 20 cm$^3$ resulting in a total volume of about 155 to 160 cm$^3$.

Although embodiments of the invention have been described using specific terms, such description is for illustrative purposes only, and it is to be understood that changes and variations obvious to the skilled artisan are to be considered within the scope of the claims that follow and their equivalents.

What is claimed is:

1. An analytical test tape instrument, comprising: an exchangeable test tape unit in the form of a tape cassette which comprises a test tape provided with a plurality of test elements to which body fluid can be applied, and a tape drive that can be coupled with the test tape unit to wind the test tape so that the test elements can be successively made available at an application site, wherein the tape drive has a direct current motor and a reduction gear unit arranged between the direct current motor and the test tape unit, wherein the tape drive has a speed controller configured to control a rotational speed of the direct current motor depending on the number of test elements of the test tape unit which have been made available.

2. The analytical test tape instrument according to claim 1, wherein the direct current motor is in the form of a mechanically commutated thin-profile rotor.

3. The analytical test tape instrument according to claim 1 wherein the reduction gear unit together with the direct current motor is encapsulated against the environment in a gear housing.

4. The analytical test tape instrument according to claim 3, wherein the direct current motor has a motor housing, the motor housing including sections formed by a housing wall of the gear housing.

5. The analytical test tape instrument according to claim 3, wherein a rotor of the direct current motor has a bearing located in the gear housing.

6. The analytical test tape instrument according to claim 3, wherein the direct current motor has a bearing for a rotor of the direct current motor located in a motor housing member and the motor housing member is clamped in the gear housing.

7. The analytical test tape instrument according to claim 3, wherein the test tape unit is positionable on an instrument chassis and the gear housing is only connected at certain points to the instrument chassis while keeping an air gap clear.

8. The analytical test tape instrument according to claim 3, wherein the direct current motor is connected via brushes to a battery-powered energy supply and brush holders are integrated in the gear housing to dampen brush vibrations.

9. The analytical test tape instrument according to claim 1, wherein a gear member of the reduction gear unit is mounted in a housing section of the direct current motor.

10. The analytical test tape instrument according to claim 9, wherein the gear member is directly coupled with the direct current motor.

11. The analytical test tape instrument according to claim 1, wherein the reduction gear unit is in the form of a toothed-wheel gear unit.

12. The analytical test tape instrument according to claim 11, wherein the toothed-wheel gear unit is a multistep spur gear unit with a laterally offset input and output.

13. The analytical test tape instrument according to claim 11, wherein the toothed-wheel gear unit includes a plurality of gear wheels that are injection-molded plastic parts.

14. The analytical test tape instrument according to claim 13, wherein the plastic parts are made from polyoxymethylene.

15. The analytical test tape instrument according to claim 1, wherein the test elements are successively spaced apart from one another along a length of the test tape and the speed controller is configured to vary the rotational speed of the direct current motor depending on the number of test elements made available at the application site such that a tape transport speed remains constant.

16. The analytical test tape instrument according to claim 15, wherein the rotational speed of the direct current motor is in a range between 100 and 200 revolutions/s and an output rotational speed of the reduction gear unit is between 0.2 and 0.5 revolutions/s.

17. The analytical test tape instrument according to claim 1, wherein the direct current motor has a motor shaft inserted into a bearing bore.

18. The analytical test tape instrument according to claim 17, wherein the motor shaft of the direct current motor includes a longitudinally slotted end section so that the slotted end section can be inserted into the bearing bore with tolerance compensation.

19. The analytical test tape instrument according to claim 17, wherein the motor shaft of the direct current motor is configured as one piece together with a drive pinion made of plastic.

20. The analytical test tape instrument according to claim 19, wherein the plastic is polyoxymethylene.

21. The analytical test tape instrument according to claim 1, further comprising a housing encasing the tape drive that encloses a constructed space of less than 150 cm$^3$.

22. The analytical test tape instrument according to claim 21, wherein the housing encloses a constructed space of less than 135 cm$^3$.

23. The analytical test tape instrument according to claim 1, wherein the tape drive is configured to rotate a take-up spool to wind up the test tape provided with the test elements.

24. An analytical test tape instrument, comprising: an exchangeable test tape unit in the form of a tape cassette which comprises a test tape provided with a plurality of test elements to which body fluid can be applied, and a tape drive that can be coupled with the test tape unit to wind the test tape so that the test elements can be successively made available at an application site, wherein the tape drive has a direct current motor and a reduction gear unit arranged between the direct current motor and the test tape unit, wherein the tape drive has a speed controller configured to control a rotational speed of the direct current motor depending on the number of test elements of the test tape unit which have been made available and the direct current motor has a motor shaft configured as one piece together with a drive pinion made of plastic.

* * * * *